Feb. 16, 1965 J. R. MITTLEIDER Plant Pat. 2,477
DIANTHUS PLANT
Filed Sept. 23, 1963
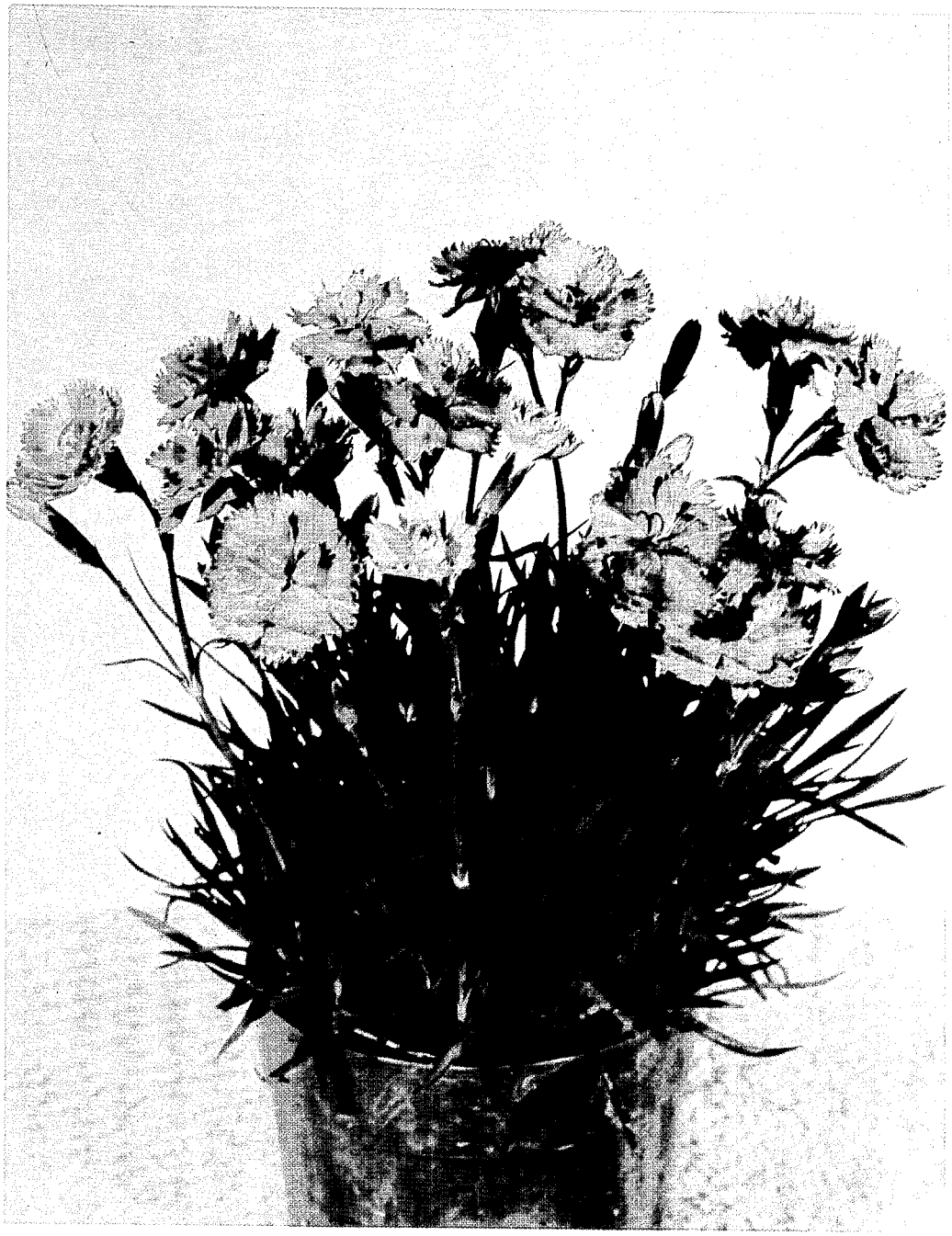
INVENTOR
JACOB R. MITTLEIDER
BY Herbert E. Fidder
AGENT United States Patent Office Plant Pat. 2,477
Patented Feb. 16, 1965

2,477
DIANTHUS PLANT

Jacob R. Mittleider, Loma Linda, Calif., assignor to Milo Academy, Inc., Milo, Oreg., a corporation of Oregon Filed Sept. 23, 1963, Ser. No. 310,961
1 Claim. (Cl. Plt.—72)

The present invention relates to a new and distinct variety of dianthus plant, which is characterized particularly by a low growing, compact densely tufted plant bearing numerous large, duplex flowers of an intense shade of magenta, and having a very faint, spicy, carnation-like fragrance.

The new and different plant variety is the result of an extensive breeding program at my nursery in Loma Linda, California, seeking new varieties of dianthus that would be especially suitable for mass plantings or edgings, without the necessity of staking the blooms. The characteristics sought were: (1) carnation foliage, (2) ever-blooming habit, (3) compactness, (4) fragrance, (5) large blooms, (6) strong stems, (7) hardiness and disease resistance, (8) pleasing new colors.

The present variety is the result of a two-step breeding program, in which Dianthus Rose Bowl (Plant Patent No. 2,034) was pollinated with pollen from a *Dianthus plumarius* of an unnamed and unpatented variety, having single to duplex flowers of a pink color. Seedlings from this first cross, selected for plant foliage, were then pollinated with pollen from a new variety of dianthus (No. 1881) developed by me, which is shown and described in co-pending application, Serial No. 310,965, filed September 23, 1963. This last-mentioned new variety of dianthus is characterized by very low growing, compact plant form and large numbers of small double flowers of a delicate rose color. The present variety was discovered among several thousand seedlings from the second cross.

The original reproduction of the plant by cuttings was carried out in the experimental section of my nursery at Loma Linda, California. Asexual reproduction of my new variety by cuttings, as performed by me at the nursery, shows that the characteristics and distinctions of the variety come true to form and are established and transmitted through succeeding propagations.

The plant grows best in well-drained, loamy soil, but is not critical as to the pH of the soil. Best blooms are obtained when the plant is grown in full sunlight.

The accompanying drawing shows a typical plant of my new variety, showing the flowers and foliage depicted in color as nearly true as it is reasonably possible to make the same in a color illustration of this character.

The following is a detailed description of my new variety, as based on my observations of specimens grown at Loma Linda, California, with color terminology and identifications in accordance with "A Dictionary of Color" by Maerz and Paul.

Plant:

*Form.*—Compact, growing to height of two to three inches.

*Growing habit.*—Densely tufted.

*Blooming habit.*—Floriferous, flowering evenly over the entire plant, with blossoms ranging from about 1½ inches in diameter to 1⅝ inches, and ranging in number from 3 or 4 on one year old plants grown in three inch pots, up to 20 or 30 on two year old plants.

*Blooming season.*—Perpetual in southern California, or wherever the mean temperature is above 50° F. Where the mean temperature drops below 50° F., the plant becomes dormant and ceases to bloom. Maximum bloom in southern California occurs from March through July, and in October and November; while minimum bloom occurs from August to October and from December through February.

*Foliage size.*—Maximum size of mature leaves on thrifty young plants is approximately three inches in length by five sixteenths of an inch in width.

*Quantity.*—Abundant.

*Shape.*—Lanceolate, or grass-like.

*Color.*—Growing under good conditions, the color of mature leaves is a deep true green, corresponding almost exactly to Aspen Green (Plate 31–C–6 in Maerz and Paul's Color Dictionary).

*Texture.*—Glaucous.

Flower:

*Size.*—The maximum size is about 1½ inches in diameter by ½ inch high.

*Borne.*—At the end of the stem.

*Stem.*—Stiff and upright, approximately 5 to 6 inches long.

*Petalage.*—Duplex.

*Color.*—The color is an intense, almost glowing magenta (Plate 52–K–12, Maerz and Paul, Magenta).

*Petals.*—Firm in texture, of obovate form with regularly crenate margins. The size of the individual petals is about ⅞ inch in length, by ¾ inch in width.

*Fragrance.*—Very faint, spicy, carnation-like.

*Calyx.*—Spreading at the tip, with acuminate teeth, and approximately 1 inch in length.

Compared to other well-known dianthus plants, this new variety is distinguished by its low-growing, bushy, compact form, usually not exceeding two to three inches in height, and bearing many faintly fragrant, duplex flowers of intense magenta color.

I claim:

A new and distinct variety of dianthus plant, substantially as shown and described herein, characterized particularly by its floriferous blooming habit, low-growing, compact, densely tufted plant form, usually not exceeding two to three inches in height, and bearing many duplex flowers of intense magenta color, said flowers having a very faint carnation-like fragrance, and being borne on the ends of stiff, upright stems.

No references cited.